United States Patent [19]

Spotorno et al.

[11] Patent Number: 5,197,988
[45] Date of Patent: Mar. 30, 1993

[54] FEMORAL PROSTHESIS

[75] Inventors: Lorenzo Spotorno, Finale Ligure, Italy; Otto Frey, Winterthur, Switzerland

[73] Assignees: Sulzer Brothers Limited, Winterthur; Protek AG, Berne, both of Switzerland

[21] Appl. No.: 528,108

[22] Filed: May 23, 1990

[30] Foreign Application Priority Data

Jun. 21, 1989 [CH] Switzerland .................... 2316/89

[51] Int. Cl.⁵ .................................. A61F 2/36
[52] U.S. Cl. ...................................... 623/23
[58] Field of Search ........................ 623/23, 18, 22

[56] References Cited

U.S. PATENT DOCUMENTS

| | | | |
|---|---|---|---|
| 3,896,505 | 9/1975 | Timmermans | 623/23 |
| 4,187,559 | 2/1980 | Grell et al. | |
| 4,292,695 | 10/1981 | Koeneman | 623/22 X |
| 4,314,381 | 2/1982 | Koeneman | 623/22 |
| 4,536,894 | 8/1985 | Galante et al. | 623/22 |
| 4,792,339 | 12/1988 | Tepi | 623/18 |
| 4,851,008 | 7/1989 | Johnson | 623/16 |
| 4,892,550 | 1/1990 | Huebsch | 623/2 |
| 4,938,774 | 7/1990 | Tepic | 623/23 |

FOREIGN PATENT DOCUMENTS

| | | | |
|---|---|---|---|
| 0220803 | 5/1987 | European Pat. Off. | |
| 2313009 | 12/1976 | France | 623/23 |
| 3212350 | 9/1988 | Japan | 623/18 |
| 0762871 | 9/1980 | U.S.S.R. | 623/22 |
| 9103991 | 4/1991 | World Int. Prop. O. | 623/22 |

Primary Examiner—Randall Green
Assistant Examiner—D. Willse
Attorney, Agent, or Firm—Kenyon & Kenyon

[57] ABSTRACT

The stem of the femoral prosthesis is provided with a slot in the medial narrow side which communicates with a through-bore within the stem adjacent to the collar. In addition, an elastomeric filling is disposed within the through-bore and cooperates with an arch which connects the proximal end of the stem to the collar or neck in order to adapt the resilience of the stem in the proximal zone to the resilience of the cortical bone. The filling may be made of polyurethane or silicone material.

2 Claims, 1 Drawing Sheet

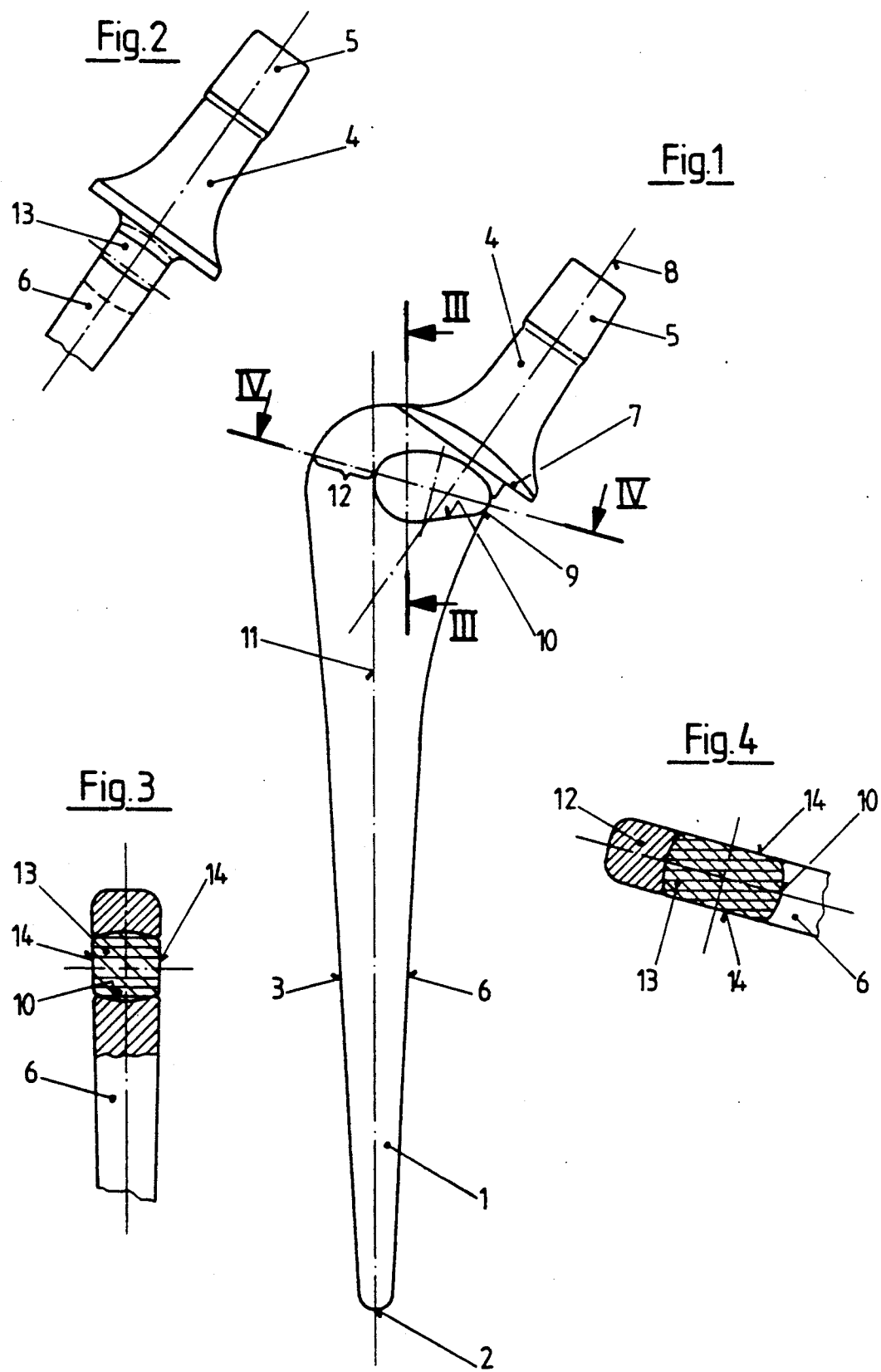

FEMORAL PROSTHESIS

This invention relates to a femoral prosthesis. More particularly, this invention relates to a Femoral Prosthesis having a fixing stem for a Femoral Head.

As is known, femoral prostheses are frequently constructed with a fixing stem for implanting in a femur, a neck for receiving a femoral head and a collar between the stem and the neck for bearing on a thigh bone (femur). It is also known that compressive stresses are very often transmitted in the proximal region from a femoral prosthesis to the thigh bone by way of the collar which separates the neck from the actual stem and which, in order to transmit forces of this kind, must bear on the cortical edge of the resection plane.

However, it has been found that because of variations in the load on the head of the joint, alternate loadings occur between the collar and the cortical bone tissue. In the course of time, these alternate loadings lead to the decomposition of the bone, and therefore, at least, to a reduction of the maximum force which can be handled.

In some cases, for example, as described in European Patent Application 0,220,803 it has been known to provide a multiple component hip femoral prosthesis with a cushioning body between a neck which rests against a cut end of a bone and a shoulder of a neck on which a femoral head is to be mounted in order to absorb forces applied by walking or other activity. Such a cushioning body is intended to dampen shocks or sudden forces and to distribute applied forces across the collar. However, such a collar does not insure an intimate and substantially constant contact between the collar and the bone during alternate loadings.

Femoral prosthesis have also been known, such as described in European Patent Application 0,308,297 wherein a proximal end of a stem is slotted in order to provide a resilient flap-like structure which can be flexed outwardly by means of a screw in order to increase bearing contact with a bone in which the stem is implanted. Other prosthesis have also been known which are formed of multiple components which utilize springs or flexures to transmit forces such as described in U.S. Pat. No. 4,187,559. However, such constructions are not relevant to the transmission of compressive forces between a collar of a femoral prosthesis and a thigh bone.

Accordingly, it is an object of the invention to provide a femoral prosthesis with a stem in which intimate and substantially constant contact between a collar and a bone is insured at virtually all the changing loadings acting on a prosthesis head.

It is another object to the invention to provide an improved femoral prosthesis for transmitting loadings to a femur.

It is another object to the invention to provide a femoral prosthesis which has a resilience similar to that of the femur bone in which the prosthesis is implanted.

Briefly, the invention provides a femoral prosthesis which is comprised of a stem for implanting in a femur, a neck for receiving a femoral head and a collar between the stem and the neck for bearing on a femur. In accordance with the invention, the stem is provided with a slot as well as a through-bore adjacent to the collar which communicates with the slot. In this respect, the slot is disposed in the medial narrow side of the stem below and near the collar and widens in the stem into the through-bore which is of bubble shape. In addition, the prosthesis is provided with an elastomeric filling in the through-bore.

If normal implantation procedure is followed, the collar of the prosthesis is preloaded into engagement with the bone tissue, particularly in the medial zone of the collar since the slot and through-bore open resiliently like jaws because of the resilience of a bridge-like arch laterally of the through-bore between a proximal end of the stem and the neck or collar.

The filling in the through-bore is made of a highly resilient material in order not to limit or restrict the resilience which is present in the proximal zone of the stem and which is determined by the lateral connection of the stem to the collar or neck. Advantageously, the depth of the through-bore laterally, and therefore, the cross-sectional area of the bridge-like arch for a given stem shape can be such as to insure adequate stem strength combined with "resilience" of the collar such as corresponds at least substantially to the resilience of the cortical bone material in response to the changing loads. Hence, the bone and the collar cover substantially the same distances as one another in their resilient "vibrations" caused by the application and removal of loads. The constancy of the engagement between the collar and the bone can therefore be improved.

Further, because of the considerable resilience of the filling, the filling yields in directions transversely to the longitudinal axis of the stem in response to compressive loads acting on the reduced volume of the filling so that the pressure the filling applies to the wall of the operation cavity increases.

Another function of the filling is to inhibit the growth and invasion of tissue into the through-bore of the stem.

The filling may be made of polyurethanes or silicones. For example, silicones and polyurethanes having a Shore A hardness of 50 to 80 and a Shore D hardness of 30 to 60 have proved to be very suitable as a material for the filling. Also, the slot in the stem may have a width of from 2 to 4 millimeters (mm) at the medial side of the stem in order to insure adequate clearance for the collar movements in response to compressive loads.

These and other objects and advantages of the invention will become more apparent from the following detailed description taken in conjunction with the accompanying drawings wherein;

FIG. 1. illustrates a side view of a femoral prosthesis constructed in accordance with the invention;

FIG. 2 illustrates a partial side view of the proximal zone of the prosthesis of FIG. 1 from the medial side;

FIG. 3 illustrates a view taken on line III—III of FIG. 1;

FIG. 4 illustrates a view taken on line IV—IV of FIG. 1.

Referring to FIG. 1, the femoral prosthesis includes a straight stem 1 for implanting in a femur (not shown). The stem 1 is made of metal, for example, a titanium alloy and widens in all directions conically from a distal end 2. The stem 1 has a lateral narrow side 3 which first merges by way of an arc into a horizontal plane, as viewed, and then terminates at a prosthesis neck 4. This neck 4 carries a conical pin 5 on which a femoral joint head (not shown) can be mounted.

The stem 1 also has a medial narrow side 6 which extends from a widening cone in a continuous curve to terminate at a collar 7 between the stem 1 and the neck 4 and which separates the stem 1 from the neck 4.

The collar 7 has a base which extends, for example, perpendicularly to a longitudinal axis 8 of the neck 4 and forms a relatively large bearing surface by means of which the collar 7 bears on the cortical tissue of the thigh bone (not shown).

The stem 1 is also provided with a slot 9 in the medial narrow side 6 a few millimeters below the collar 7, as viewed. This slot 9 widens in the lateral direction into an oval shaped through-bore 10 in the stem 1. In the example shown, the through-bore 10 extends towards the large trochanter approximately as far as the longitudinal center plane 11 of the stem 1. As shown in FIG. 1, the through-bore 10 defines an arch or connection 12 which connects a proximal portion of the stem 1 to the collar 7 or neck 4. As indicated in FIG. 4, the bridge-like arch 12 is of a substantially square cross-section. The shape and dimensions of this arch 12 are determined by the required minimum strength of the stem 1 and by the required "resilience" of the collar 7 which should be adapted to the resilience of the cortical bone tissue.

Referring to FIGS. 3 and 4, the through-bore 10 is filled up with a highly resilient elastomeric filling 13, for example, made of polyurethane. As also indicated, the external surfaces 14 of the filling 13 which are exposed to and which bear on the bone within a bone cavity (now shown) are provided with a coating, for example, of hydroxylapatite in order to promote the in growth of tissue. Similarly, the base of the collar 7 engaging in the bone may have a structure to promote the in growth of bone tissue.

As indicated in FIGS. 3 and 4, the walls which define the through-bore 10 are of curvilinear shape in a transverse direction.

The invention thus provides a femoral prosthesis in which the resilience of a stem is adapted in the proximal zone to the resilience of the cortical bone. In addition, an intimate and constant contact is insured between the prosthesis collar which bears on the cortical edge of the resection plane of the bone and the bone cortex.

What is claimed is:

1. A prosthesis comprising
   a stem for implanting in a femur including a medial surface;
   a neck for receiving a femoral head;
   a collar between said stem and said neck for bearing on a femur;
   a slot in said medial surface of said stem adjacent said collar;
   a throughbore extending from said medial side laterally to a longitudinal center plane of said stem and in said stem and communicating with said slot, wherein said throughbore is oval-shaped; and
   a resilient filling in said throughbore.

2. A prosthesis comprising
   a straight stem for implanting in a femur and including a medial surface;
   a neck for receiving a femoral head;
   a collar separating said stem from said neck;
   a throughbore in said stem adjacent said collar and extending from said medial surface laterally of said stem to define an arch connecting a proximal portion of said stem to said collar, wherein said arch is of square cross-section; and
   a resilient filling in said throughbore.

* * * * *

UNITED STATES PATENT AND TRADEMARK OFFICE
CERTIFICATE OF CORRECTION

PATENT NO. : 5,197,988

DATED : March 30, 1993

INVENTOR(S) : Spotorno et al.

It is certified that error appears in the above-identified patent and that said Letters Patent is hereby corrected as shown below:

```
Column 1, line 35,   change "prosthesis" to --prostheses--;
         line 41,   change "prosthesis" to --prostheses--;

Column 3, line 7,    change "oval shaped" to --oval-shaped--;
         line 25,   change "now" to --not--;
         line 26,   change "in growth" to --ingrowth--;
         line 28,   change "in growth" to --ingrowth--.
```

Signed and Sealed this

Seventh Day of June, 1994

*Attest:*

BRUCE LEHMAN

*Attesting Officer*     *Commissioner of Patents and Trademarks*